United States Patent [19]

Murahashi et al.

[11] Patent Number: 4,942,220

[45] Date of Patent: Jul. 17, 1990

[54] PROCESS FOR PREPARING POLY-AMIDE FROM NITRILE AND AMINE WITH CATALYTIC COMPLEX

[75] Inventors: Shunichi Murahashi, Ikeda; Takeshi Naota, Kawanishi, both of Japan

[73] Assignee: Osaka University, Suita, Japan

[21] Appl. No.: 67,414

[22] Filed: Jun. 19, 1987

Related U.S. Application Data

[60] Division of Ser. No. 838,199, Mar. 7, 1986, Pat. No. 4,801,748, which is a continuation-in-part of Ser. No. 828,245, Feb. 11, 1986, abandoned.

[30] Foreign Application Priority Data

Mar. 8, 1985 [JP] Japan .................................. 60-44939

[51] Int. Cl.$^5$ .............................................. C08G 69/28
[52] U.S. Cl. ...................................... 528/336; 528/310; 528/312; 528/313; 528/315; 528/318; 528/319; 528/341; 528/346; 528/347
[58] Field of Search ........................................... 528/336

[56] References Cited

U.S. PATENT DOCUMENTS

| | | | |
|---|---|---|---|
| Re. 28,288 | 2/1974 | Goetz et al. ......................... | 564/126 |
| 2,280,578 | 4/1942 | Hanford . | |
| 2,421,030 | 5/1947 | Mahan ................................. | 564/126 |
| 3,040,095 | 6/1962 | Gilbert et al. ...................... | 564/126 |
| 3,366,639 | 1/1968 | Haefele ................................ | 564/126 |
| 3,597,481 | 8/1971 | Tefertiller et al. ................. | 564/126 |
| 3,670,021 | 6/1972 | Goetz et al. ........................ | 564/126 |
| 3,673,250 | 6/1972 | Rauch et al. ....................... | 564/236 |
| 3,758,576 | 9/1973 | Takahashi . | |
| 3,794,682 | 2/1974 | Barger ................................. | 564/126 |
| 3,825,596 | 7/1974 | Naito et al. ..................... | 260/558 R |
| 3,847,876 | 11/1974 | Onsager ............................... | 528/336 |
| 3,948,989 | 4/1976 | Drake ................................... | 260/561 |
| 4,036,879 | 7/1977 | Habermann ......................... | 564/126 |
| 4,060,553 | 11/1977 | Redmore et al. ................... | 260/559 |
| 4,329,500 | 5/1982 | Habermann ......................... | 564/126 |
| 4,380,623 | 4/1983 | Greene et al. ...................... | 528/336 |
| 4,436,898 | 3/1984 | Hofmann et al. ................... | 528/336 |
| 4,490,521 | 12/1984 | Coffey et al. ....................... | 528/336 |
| 4,501,881 | 2/1985 | Greene et al. ...................... | 528/336 |
| 4,520,190 | 5/1985 | Coffey et al. ....................... | 528/336 |
| 4,542,205 | 9/1985 | Curatolo et al. ................... | 528/336 |
| 4,543,407 | 9/1985 | Curatolo et al. ................... | 528/336 |
| 4,554,345 | 11/1985 | Greene et al. ...................... | 528/336 |
| 4,603,192 | 7/1986 | Coffey et al. ....................... | 528/336 |
| 4,801,748 | 1/1989 | Murahashi et al. ................. | 528/336 |

FOREIGN PATENT DOCUMENTS

| | | |
|---|---|---|
| 0070424 | 6/1982 | European Pat. Off. . |
| 45-21805 | 9/1970 | Japan . |
| 45-35283 | 11/1970 | Japan . |
| 48-31086 | 9/1973 | Japan . |

*Primary Examiner*—Harold D. Anderson
*Attorney, Agent, or Firm*—Spencer & Frank

[57] ABSTRACT

Polyamides are prepared from a carbonitrile and an amine by reacting by heating a mixture of a carbonitrile which is a dinitrile, an equivalent amount of a primary or secondary amine which is a diamine, and at least a stoichiometric amount of water in the presence of an effective amount of a catalyst. The catalyst is a complex containing at least one metal selected from the group consisting of ruthenium, rhodium and molybdenum, and at least one group selected from the group consisting of hydride, phosphine, carbonyl, ammonia, and hydroxyl. The polyamine has a recurring unit represented by the general formula:

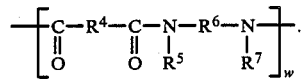

11 Claims, No Drawings

PROCESS FOR PREPARING POLY-AMIDE FROM NITRILE AND AMINE WITH CATALYTIC COMPLEX

This is a Division of application Ser. No. 06/838,199 filed Mar. 7, 1986, for which U.S. Pat. No. 4,801,748 issued on Jan. 31, 1989, and which is a Continuation-In-Part of application Ser. No. 06/828,245 filed Feb. 11, 1986, now abandoned.

BACKGROUND OF THE INVENTION

1. Field of the Invention

This invention relates to a novel process for preparing amides from nitriles and amines, and more particularly to a process for preparing amides directly from nitriles and amines using ruthenium compounds, etc. as a catalyst, and further relates to a process for preparing polyamides directly from dinitriles and diamines or from aminonitriles. 2. Background of the Art.

Many kinds of amide compounds including polyamides have been developed and used in various industrial fields to date. These are particularly useful as materials for synthetic fibers and plastic molds, dyeability improvers or antistatic agents therefor, finishing or sizing agents for yarns and textiles, surfactants, coagulants, adhesives, organic solvents, plastics foaming agents, printing ink additives, dyestuffs, organic pigments, pharmaceuticals, agricultural chemicals, livestock feeds, intermediates thereof, etc.

Heretofore, when an amide was synthesized from a nitrile and an amine, a process in which the nitrile is hydrolized and thereby converted into carboxylic acid which is subsequently condensed with the amine has been generally adopted.

However, when such a conventional manufacturing process has been commercially practised, various problems have been encountered related to an increased number of process steps, separation of products in each step, equipment for preventing pollution caused by by-products, the cost of production, etc.

SUMMARY OF THE INVENTION

The present invention, differs from the conventional process and is directed to provision of a process with a minimal number of steps for synthesizing amides directly from nitriles and amines, whereby curtailment of reaction time, compaction of equipment and clean operations are realized.

Further, the present invention is aimed at developing the above-mentioned direct synthesis of amides into a direct synthesis of polyamides with similar advantages.

As a result of assiduous research to solve the aforementioned problems, we, the inventors, have unexpectedly found that these objects can be attained efficiently by using a catalyst, such as a ruthenium compound and the like, as explained hereinafter, and to accomplish the objects of the present invention.

Namely, the present invention is a novel process for preparing amides from nitriles and amines which comprises reacting by heating a mixture of a carbonitrile, an equivalent amount of a primary or secondary amine and at least the stoichiometric amount of water, to form an amide.

In this invention, the term "carbonitrile" or "nitrile" is intended to mean an organic compound having at least one cyano group in its molecule, and the term "amine" an organic compound having at least one amino group. Both the cyano group and the amino group may be comprised in one molecule, constituting an aminonitrile compound. Further, the term "amide" is intended to mean an organic compound having at least one amide linkage in its molecule, including a socalled polyamide.

The present invention includes the following three principal embodiments.

The first embodiment of the invention comprises reacting a nitrile represented by the general formula:

$$R^1CN$$

where $R^1$ denotes a monovalent residue of: a saturated or unsaturated aliphatic hydrocarbon; a group derived from the said aliphatic hydrocarbon by substituting an aromatic group for its hydrogen atom; an alicyclic hydrocarbon; an aromatic hydrocarbon; a heterocycle; or an aliphatic hydrocarbon having a heterocyclic ring rest- or heteroatom-containing substituent,
with an amine and water, which amine is represented by the general formula $$R^2R^3NH$$

where $R^2$ and $R^3$ are same with or different from each other and respectively denote hydrogen atom or a monovalent residue of: a saturated or unsaturated aliphatic hydrocarbon; a group derived from the said aliphatic hydrocarbon by substituting an aromatic group for its hydrogen atom; an alicyclic hydrocarbon; an aromatic hydrocarbon; a heterocycle; or an aliphatic hydrocarbon having a heterocyclic ring rest- or heteroatom-containing substituent, and then $R^2$ and $R^3$ may be bridged by carbon atom or a heteroatom, forming a saturated or unsaturated ring, in the presence of a catalyst, to form an amide represented by the following general formula:

$$R^1\underset{\underset{O}{\|}}{C}NR^2R^3$$

where $R^1$, $R^2$ and $R^3$ are same as defined above.

More particularly, $R^1$ may denote an alkyl, alkenyl, alkynyl, cycloalkyl or aryl group having up to 20 carbon atoms, or a monovalent residue of 3 to 7 membered heterocyclic group having in the ring up to 3 heteroatoms selected from O, N and S, with a proviso that at least one hydrogen of the above group may be substituted with an aryl, alkenyl or alkynyl group having up to 12 carbon atoms, a monovalent residue of 3 to 7 membered heterocyclic group, OR, CO$^2$R, NR$_2$, SR, SiR$_3$ or CONR$_2$ group wherein R represents an optionally substituted alkyl group having up to 10 carbon atoms, or phenyl group. Further, $R^2$ and $R^3$ may be the same or different, and respectively represent a hydrogen atom or have the same meaning as $R^1$ previously defined, and then $R^2$ and $R^3$ may be bridged by a carbon atom or a heteroatom selected from O, N and S, forming a saturated or unsaturated ring.

Further, the second principal embodiment of the invention comprises reacting at least one dinitrile represented by the general formula:

$$R^4(CN)_2$$

where $R^4$ denotes a bivalent residue of: a saturated or unsaturated aliphatic hydrocarbon; a group derived from the said aliphatic hydrocarbon by substituting an aromatic or heterocyclic ring rest- or a heteroatom-containing group for its hydrogen atom; an alicyclic hydrocarbon; an aromatic hydrocarbon; a heterocycle; or a group consisting of two aliphatic hydrocarbon moieties bridged by an aromatic group, heterocycle or heteroatom, with at least one diamine and water, which diamine is represented by the general formula:

$$HN(R^5)-R^6-(R^7)NH$$

where $R^5$ and $R^7$ are same with or different from each other and respectively denote hydrogen atom or a monovalent residue of: a saturated or unsaturated aliphatic hydrocarbon; a group derived from the said aliphatic hydrocarbon by substituting an aromatic group for its hydrogen atom; an alicyclic hydrocarbon; an aromatic hydrocarbon; a heterocycle; or an aliphatic hydrocarbon having a heterocyclic ring rest- or heteroatom-containing substituent, and $R^6$ denotes a bivalent residue of: a saturated or unsaturated aliphatic hydrocarbon; a group derived from the said aliphatic hydrocarbon by substituting an aromatic or heterocyclic ring rest- or a heteroatom-containing group for its hydrogen atom; an alicyclic hydrocarbon, an aromatic hydrocarbon, a heterocycle; or a group consisting of two aliphatic hydrocarbon moieties bridged by an aromatic group, heterocycle or heteroatom, in the presence of a catalyst, to form a polyamide having a recurring unit represented by the following general formula:

$$\left[\begin{array}{c} C-R^4-C-N-R^6-N \\ \parallel \quad\quad \parallel \quad | \quad\quad\quad | \\ O \quad\quad O \quad R^5 \quad\quad R^7 \end{array}\right]_w$$

where w is an integer and $R^4$, $R^5$, $R^6$ and $R^7$ are the same as defined above.

More particularly, $R^4$ may denote an alkylene, alkenylene, alkynylene, cycloalkylene or arylene group having up to 20 carbon atoms; a bivalent residue of 3 to 7 membered heterocyclic group having in the ring up to 3 heteroatoms selected from O, N and S; or a group consisting of two aliphatic hydrocarbon moieties each having up to 10 carbon atoms bridged by phenylene group; a bivalent residue of 3 to 7 membered heterocyclic group having in the ring up to 3 heteroatoms selected from O, N and S, or such a heteroatom itself; with a proviso that at least one hydrogen of the above group may be substituted with an aryl, alkenyl or alkynyl group having up to 12 carbon atoms, a monovalent residue of 3 to 7 membered heterocyclic group, OR, $CO_2R$, $NR_2$, SR, $SiR_3$ or $CONR_2$ group where R represents an optionally substituted alkyl group having up to 10 carbon atoms, or phenyl group. Further, $R^5$ and $R^7$ may be the same or different, and respectively represent a hydrogen atom or have the same meaning as $R^1$ previously defined, and $R^6$ has the same meaning as $R^4$ previously defined.

Furthermore, the third embodiment of the invention comprises reacting at least one aminonitrile with water in the presence of a catalyst, said aminonitrile being represented by the following general formula:
$$HN(R^5)-R^6-CN$$

where $R^5$ denotes hydrogen atom or a monovalent residue of: a saturated or unsaturated aliphatic hydrocarbon; a group derived from the said aliphatic hydrocarbon by substituting an aromatic group for its hydrogen atom; an alicyclic hydrocarbon; an aromatic hydrocarbon; a heterocycle; or an aliphatic hydrocarbon having a heterocyclic ring rest- or heteroatom-containing substituent, and $R^6$ denotes a bivalent residue of: a saturated or unsaturated aliphatic hydrocarbon; a group derived from the said aliphatic hydrocarbon by substituting an aromatic or heterocyclic ring rest- or a heteroatom-containing group for its hydrogen atom; an alicyclic hydrocarbon; an aromatic hydrocarbon; a heterocycle; or a group consisting of two aliphatic hydrocarbon moieties bridged by an aromatic group, heterocycle or heteroatom, to form a polyamide having a recurring unit represented by the following general formula:

$$\left[\begin{array}{c} N-R^6-C \\ | \quad\quad\quad \parallel \\ R^5 \quad\quad O \end{array}\right]_y$$

where y is an integer and $R^5$ and $R^6$ are the same as defined above.

More particularly, $R^5$ may represent a hydrogen atom or have the same meaning as $R^1$ previously defined. Further, $R^6$ may have the same meaning as $R^4$ previously defined.

DESCRIPTION OF THE PREFERRED EMBODIMENTS

As nitriles to be employed in the first embodiment, mention may be made of, for instance, acetonitrile, propionitrile, butyronitrile, acrylonitrile, methacrylonitrile, 2-methyl-2-butenenitrile, 2-pentenenitrile, 3-pentenenitrile, cinnamonitrile, cyclohexanecarbonitrile, benzonitrile, 2-thiazolecarbonitrile, methoxyacetonitrile, etc. Further, when the reacting amine is a monoamine, nitriles having two or more cyano groups, such as 1,4-dicyanobutane, 1,6-dicyanohexane, methylglutaronitrile and the like may be included in the first embodiment.

As amines to be used in the first embodiment, mention may be made of, for instance, methylamine, ethylamine, butylamine, diethylamine, benzylamine, benzylmethylamine, cyclohexylamine, aniline, 2-benzofuranamine, anisidine, pyrrolidine, piperidine, morpholine and the like. Further, when the reacting nitrile is a mononitrile, amines having two or more amino groups such as hexamethylenediamine, 1,2-diaminocyclohexane and piperazine having two amino groups, bis-hexamethylenetriamine having three amino groups and the like may be included in the first embodiment.

In the second embodiment, preferable dinitriles are alkylenedinitriles having the general formula:

$$NC(CH_2)_nCN$$

where n is an integer ranging from 1 to 20, while preferable diamines are alkylenediamines having the general formula:

$$HN(R^5)-(CH_2)_m-NHR^7$$

where m is an integer ranging from 1 to 20, and from those reactants are obtained polyamides having a recurring unit represented by the general formula:

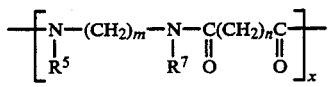

wherein $R^5$ and $R^7$ are as defined hereinabove and x is an integer.

In the third embodiment, preferable aminonitriles are aminoalkylnitriles having the general formula:

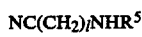

where l is an integer ranging from 1 to 3 or from 5 to 20, from which will result polyamides having a recurring unit represented by the general formula:

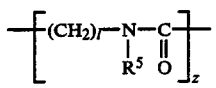

wherein $R^5$ is as defined hereinabove and z is an integer.

In the second and third embodiments, two or more dinitriles and/or diamines and two or more aminonitrites may be employed respectively and in these cases copolyamides will be obtained. Besides, in each case, nitriles and/or amines and aminonitriles which are respectively tri- or greater than tri-functional also can be added in such a manner that nearly stoichiometric proportion as a whole are attained, if required, in order to improve properties of the resulting polyamides.

Needless to say, as a polymerization inhibitor, a small amount of monoamine, mononitrile or monocarboxylic acid may be added to the reaction mixture in the second and third embodiments of the invention, in order to control the polymer viscosity.

The amide-forming reaction in the process of the invention can be facilitated by addition of a catalyst to the reaction system. The catalysts employable in the present invention include ruthenium-, zinc-, rhodium-, titanium-, chromium-, zirconium-, osmium-, nickel-, cobalt-, molybdenum-, palladium-, selenium-, iron-, copper-, lead-, mercury-, vanadium-, cadmium-, iridium- and platinum-compounds, such as complexes thereof with at least one group selected from the group consisting of hydride, phosphine, carbonyl, ammonia and hydroxyl, carbonyl compounds, halides and oxides of these metals or the like. Among the above metal compounds, at least one selected from the group consisting of ruthenium-, rhodium-, nickel-, molybdenum-, copper-, zinc- and cobalt-compounds are preferable, and further, ruthenium complexes, ZnCl and $MO(CO)_6$ are more preferable and particularly $RuH_2(PPh_3)_4$, $RuH_2(CO)(PPh_2)_3$ and the like (where Ph represents a phenyl group) are most preferable on account of their high activity.

These catalyst may be used alone or in combination and further, if required, along with an appropriate promoter such as a metal hydroxide.

As to an amount of catalyst to be added, only a catalytic amount existing in the reaction system may be enough and a preferable amount is, for instance, in the range between about 0.001 and about 10 mol %, more preferably between about 0.1 and about 3 mol %, based on the starting material nitrile, but with a smaller or larger amount, the reaction can be effected.

In the present invention, it is preferred that the reaction be carried out in an inert gas. Although the reaction readily proceeds on addition of only the catalyst to amines, nitriles (or aminonitriles) and water, the reaction will be carried out more effectively in the presence of a water-miscible organic solvent such as 1,2-dimethoxyethane, dioxane, pyridine, diglyme, tetrahydrofuran and the like. Though the reaction temperature has no specified upper limit, not higher than 250° C. is preferable. The reaction pressure may be atmospheric or higher, if required. The amount of water required is a stoichiometric amount based on the amount of nitrile. One equivalent of water, based on the nitrile is sufficient, however, there may be some excess of water, that is, from 1–100 equivalents, and, preferably, in the range of 1–3 equivalents.

Some of the preferred embodiments of the present invention will be illustrated by way of the following examples.

EXAMPLE 1

Synthesis of N-butylacetamide

Into a test tube of 30 ml capacity, a magnetic stirrer was put and argon gas was admitted to displace the air. Acetonitrile (2.0 mmol), butylamine (2.2 mmol), water (4.0 mmol,), $RuH_2(PPh_3)_4$ (0.06 mmol) and 1,2-dimethoxyethane (DME, 0.5 ml) were placed in the test tube that was thereafter sealed.

The solution was allowed to react at 160° C. for 24 hours while stirring. After cooling to −78° C., the sealed tube was opened and the product was isolated by passing through a short Florisil ® column. N-butylacetamide was obtained in a 93% yield. Identification of N-butylacetamide was conducted by means of IR, NMR and mass spectrum data.

EXAMPLES 2-23

Examples wherein reaction was carried out under the same conditions as Example 1 are shown in Table 1.

TABLE 1(a)

| Example No. | Nitrile | Amine | Product*3 | Yield*4 (%) |
|---|---|---|---|---|
| 2 | CH₃CN | BuNH₂*1 | CH₃CNHBu*1 (O=) | 93 |
| 3 | CH₃CN | (morpholine, NH) | CH₃CN—(morpholine, O) | 99 |

TABLE 1(a)-continued

| Example No. | Nitrile | Amine | Product*3 | Yield*4 (%) |
|---|---|---|---|---|
| 4 | $CH_3CN$ | cyclohexyl-$NH_2$ | $CH_3C(=O)NH$-cyclohexyl | 84 |
| 5 | $CH_3CN$ | $PhCH_2NH_2$ | $CH_3C(=O)NHCH_2Ph$ | 98 |
| 6 | $CH_3CN$ | $PhCH_2NHCH_3$ | $CH_3C(=O)N(CH_3)CH_2Ph$ | 95 |
| 7 | $CH_3CN$ | $PhNH_2$ | $CH_3C(=O)NHPh$ | 55 |
| 8 | $CH_3CN$*2 | $H_2N(CH_2)_6NH_2$ | $CH_3C(=O)NH(CH_2)_6NHC(=O)CH_3$ | 89 |
| 9 | $C_3H_7CN$ | piperidine | $C_3H_7C(=O)N$-piperidinyl | 90 |
| 10 | $CH_3OCH_2CN$ | $BuNH_2$ | $CH_3OCH_2C(=O)NHBu$ | 93 |
| 11 | $CH_3OCH_2CN$ | piperidine | $CH_3OCH_2C(=O)N$-piperidinyl | 87 |
| 12 | $PhCH=CHCN$ | piperidine | $PhCH=CHC(=O)N$-piperidinyl | 57 |
| 13 | $PhCN$ | piperidine | $PhC(=O)N$-piperidinyl | 50 |
| 14 | $NC(CH_2)_2CN$ | pyrrolidine*2 | pyrrolidinyl-$C(=O)(CH_2)_2C(=O)$-pyrrolidinyl | 91 |
| 15 | $CH_3CN$ | $Bu_2NH$ | $CH_3C(=O)NBu_2$ | 61 |
| 16 | $CH_3CN$ | 1,2,3,4-tetrahydroisoquinoline (NH) | 2-acetyl-1,2,3,4-tetrahydroisoquinoline (N—$C(=O)CH_3$) | 59 |
| 17 | $CH_3CN$*5 | $H_2N(CH_2)_4NH(CH_2)_3NH_2$ | $CH_3C(=O)NH(CH_2)_4N(COCH_3)(CH_2)_3NHC(=O)CH_3$ | 75 |

TABLE 1(a)-continued

| Example No. | Nitrile | Amine | Product*3 | Yield*4 (%) |
|---|---|---|---|---|
| 18 | (CH$_3$)$_2$CHCN | CH$_2$=CHCH$_2$NH$_2$ | (CH$_3$)$_2$CHC(O)NHCH$_2$CH=CH$_2$ | 32 |
| 19 | cyclohexenyl-CH$_2$CN | CH$_2$OCH$_2$CH$_2$NH$_2$ | cyclohexenyl-CH$_2$C(O)NHCH$_2$CH$_2$OCH$_3$ | 54 |
| 20 | norbornenyl-CN | piperidinyl-N—CH$_2$CH$_2$NH$_2$ | norbornenyl-C(O)NHCH$_2$CH$_2$N(piperidinyl) | 41 |
| 21 | CH$_3$OC(O)CH$_2$CH$_2$CN | (CH$_3$)$_2$CHNH$_2$ | CH$_3$OC(O)CH$_2$CH$_2$C(O)NHCH(CH$_3$)$_2$ | 38 |
| 22 | PhCN | BuNH$_2$ | PhC(O)NHBu | 30 |
| 23 | furyl-CN | CH$_3$CH$_2$OC(O)(CH$_2$)$_5$NH$_2$ | furyl-C(O)NH(CH$_2$)$_5$C(O)OCH$_2$CH$_3$ | 32 |

*1Bu: butyl group.
*2 2 equivalent.
*3Each product was identified by IR, NMR and mass spectrum data.
*4Isolated yield.
*5 5 equivalent.

Although a ruthenium compound was used as the catalyst in Examples enumerated above, it was confirmed that amides were also obtainable using rhodium-, nickel- and molybdenum-compounds in lieu of the ruthenium compound.

EXAMPLES 24–45

The catalyst, RuH$_2$(PPh$_3$)$_4$ used in the reaction in Example 1 was replaced by the under-mentioned 22 compounds and respective series of the reaction were carried out to obtain N-butylacetamide in yields and with the acetonitrile conversions respectively given in Table 2 below.

TABLE 2

| Example No. | Catalyst | Conversion (%) | Yield$^a$ (%) |
|---|---|---|---|
| 24 | RuH$_2$(PPh$_3$)$_4$ | 100 | 99$^b$ |
| 25 | RuH$_2$(CO)(PPh$_3$)$_3$ | 100 | 100 |
| 26 | [Ru(NH$_3$)$_5$Cl]Cl$_2$ | 54 | 90 |
| 27 | Rh(CO)(OH)(PPh$_3$)$_2$ *1 | 41 | 51 |
| 28 | Ni(piaH)$_2$·Cl$_2$·2H$_2$O | 43 | 23 |
| 29 | PdCl$_2$ | 39 | 42 |
| 30 | Fe(CO)$_5$ | 17 | 15 |
| 31 | Mo(CO)$_6$ | 66 | 77 |
| 32 | Cu(O) | 30 | 33 |
| 33 | Al(OH)$_2$(C$_{17}$H$_{35}$CO$_2$) | 8 | 25 |
| 34 | Ti(Oi-Pr)$_4$ | 17 | 99 |
| 35 | VO(AcAc)$_2$ | 60 | 5 |
| 36 | Cr(CO)$_6$ | 9 | 99 |
| 37 | CoSO$_4$·7H$_2$O | 34 | 12 |
| 38 | ZnCl$_2$ | 76 | 99 |
| 39 | SeO$_2$ | 13 | 52 |
| 40 | ZrCl$_2$Cp$_2$ | 21 | 98 |
| 41 | CdCl$_2$ | 52 | 20 |
| 42 | IrCl$_3^-$ | 77 | 10 |
| 43 | PtO$_2$ | 20 | 3 |
| 44 | HgCl$_2$ | 34 | 36 |
| 45 | Pb(OAc)$_4$ | 36 | 49 |

*1: Picolinic acid amide
$^a$GLC yield based on acetonitrile
$^b$Isolated yield.

EXAMPLE 46

Synthesis of nylon-66

Adiponitrile (0.216 g), hexamethylenediamine (0.232 g), RuH$_2$(PPh$_3$)$_4$ (0.069 g), water (0.072 g) and 1,2-dimethoxyethane (0.5 ml) were reacted in an argon gas atmosphere in a sealed tube under the same conditions as Example 1. After the reaction, precipitates were separated by filtration, washed with chloroform and dried. Then, nylon-66 was obtained in a 92% yield. Its number average molecular weight was 4,100 which was calculated from terminal amino-groups quantified by p-toluene sulfonic acid using thymol blue as an indicator. The nylon-66 was identified by IR (KBr) spectrum which showed absorptions at 3,230 (N—H, m), 2,910 (C—H, s), 2,840 (s), 1,630 (C=O, s), 1,530 (N—H, s), 1,225 (w) and 740 (w) cm$^{-1}$; and by $^1$HNMR spectrum (HCO$_2$H, 60 MHz): δ 0.93–1.85 (m, 12H, —CH$_2$—), 1.95–2.60 (m, 4 H, —COCH$_2$—), 2.82–3.43 (m, 4 H, —N—CH$_2$—) and 8.45 (br.s, 2 H, —NH).

EXAMPLE 47

Synthesis of high molecular weight nylon-66

Adiponitrile (0.216 g), hexamethylenediamine (0.232 g), $RuH_2(PPh_3)_4$ (0.069 g), water (0.072 g) and 1,2-dimethoxyethane (0.5 ml) were reacted at 200° C. in an argon gas atmosphere for 24 hours in a sealed tube. After the reaction, precipitates were separated by filtration, washed with chloroform and dried. Then, nylon-66 having a melting point temperature higher than 255° C. was obtained in a 98% yield. Its infrared and $^1H$ NMR spectra similar to those in Example 46 resulted. The number average molecular weight was 8,900 which was calculated from terminal amino groups quantified by p-toluene sulfonic acid using thymol blue as an indicator (with respect to the polymer solution in cresol).

EXAMPLE 48

Synthesis of nylon-2,6

Adiponitrile (0.216 g), ethylenediamine (0.120 g), $RuH_2(PPh_3)_4$ (0.069 g), water (0.072 g) and 1,2-dimethoxyethane (0.5 ml) were reacted in a sealed tube under the same conditions as Example 1. After the reaction, precipitates were separated by filtration, washed with chloroform and dried. Then, nylon-2,6 was obtained in a 99% yield. Its number average molecular weight was 3,700 which was calculated from terminal amino groups quantified by p-toluene sulfonic acid using thymol blue as an indicator. Its infrared (KBr) spectrum showed absorptions at 3,350 (N—H, s), 3,170 (N—H, s), 2,950 (C—H, s), 1,645 (C=O, s), 1,545 (N—H, m), 1,330 (m), 1,120 (m) and 800 (m) $cm^{-1}$; and $^1H$ NMR spectrum ($HCO_2H$, 60 MHz): δ 1.03–1.96 (m, 4 H, —$CH_2$—), 1.96–2.68 (m, 4 H, —$COCH_2$—), 3.05–3.95 (m, 4 H, —N—$CH_2$—) and 8.22 (br.s, 2H, —NH).

EXAMPLE 49

Synthesis of nylon-3

3-Aminopropionitrile (0.282 g), water (0.145 g), $RuH_2(PPh_3)_4$ (0.069 g) and 1,2-dimethoxyethane (0.5 ml) were reacted at 200° C. in an argon gas atmosphere for 24 hours in a sealed tube. After the reaction, precipitates were separated by filtration, washed with chloroform and dried. Then, nylon-3 was obtained in a 98% yield. Its number average molecular weight was 1,600 which was calculated in the same manner as described in Example 48. Its infrared (KBr) spectrum showed absorptions at 3,290 (N—H, s), 2,940 (C—H, w), 1,640 (C=O, s), 1,545 (N—H, s), 1,435 (m), 1,115 (m) and 695 (m) $cm^{-1}$; and $^1H$NMR spectrum ($HCO_2H$, 60 MHz): δ 1.78–2.98 (m, 2 H, —$COCH_2$—), 3.05–4.14 (m, 2 H, N—$CH_2$—) and 7.56 (br.s, 1 H, —NH).

EXAMPLE 50

Synthesis of nylon-12

12-Aminoundecanenitrile (0.393 g), water (0.072 g), $RuH_2(PPh_3)_4$ (0.069 g) and 1,2-dimethoxyethane (0.5 ml) were reacted in an argon gas atmosphere in a sealed tube under the same conditions as Example 1. After the reaction, precipitates were separated by filtration, washed with chloroform and dried. Then, nylon-12 was obtained in a 99% yield. Its number average molecular weight was 5,000 which was calculated in the same manner as described in Example 48. Its infrared (KBr) spectrum showed absorptions at 3,290 (N—H, s), 2,940 (C—H, w), 1,640 (C=O, s), 1,545 (N—H, s), 1,435 (m), 1,115 (m) and 695 (m) $cm^{-1}$; and $^1H$ NMR ($HCO_2H$, 60 MHz): δ 0.93–1.85 (m, 18 H, —$CH_2$—), 1.95–2.60 (m, 2 H, —$COCH_2$—), 2.82–3.43 (m, 2 H, —N—$CH_2$—) and 8.45 (br.s, 2 H, —NH).

EXAMPLE 51

Synthesis of nylon-6T

Terephthalonitrile (0.256 g), hexamethylenediamine (0.232 g), $RuH_2(PPh_3)_4$ (0.069 g), water (0.074 g) and 1,2-dimethoxyethane (0.5 ml) were reacted at 180° C. in an argon gas atmosphere for 24 hours in a sealed tube. After the reaction, precipitates were separated by filtration, washed with chloroform and dried. Then, polyhexamethyleneterephthalamide having a decomposition temperature of 265° C. was obtained in a 98% yield. Its number average molecular weight was 1,200 which was calculated in the same manner as described in Example 48. Its infrared (KBr) spectrum showed absorptions at 3,160 (N—H, s), 3,070 (C—H, m), 2,920 (C—H, S), 2,860 (C—H, m), 1,620 (C=O, s), 1,535 (N—H, m), 1,410 (m), 1,285 (m) and 860 (m) $cm^{-1}$; and $^1H$ NMR ($HCO_2H$, 60 MHz): δ 0.71–2.34 (m, 8 H, —$CH_2$—), 2.90–3.76 (m, 4 H, —$NCH_2$), 6.21 (br.s, 2 H, NH) and 7.00–7.54 (m, 4 H, ArH).

EXAMPLE 52

Synthesis of poly-p-cyclohexaneadipamide

Adiponitrile (0.216 g), 1,4-cyclohexanediamine (0.228 g), $RuH_2(PPh_3)_4$ (0.069 g), water (0.074 g) and 1,2-dimethoxyethane (0.5 ml) were reacted at 180° C. in an argon gas atmosphere for 24 hours in a sealed tube. After the reaction, precipitates were separated by filtration, washed with chloroform and dried. Then, polyamide having a decomposition temperature of 208° C. was obtained in a 98% yield. Its number average molecular weight was 1,000 which was calculated in the same manner as described in Example 48. Its infrared (KBr) spectrum showed absorptions at 3,180 (N—H, s), 2,925 (C—H, s), 2,860 (C—H, m), 1,630 (C=O, s), 1,540 (N—H, s), 1,410 (m), 1,115 (m) and 745 (m) $cm^{-1}$; and $^1H$ NMR ($HCO_2H$, 60 MHz): δ 0.84–1.97 (m, 16 H), 2.70–3.27 (m, 2 H, —NCH'—) and 6.76 (br.s, 2 H, NH).

EXAMPLE 53

Synthesis of polypiperazineadipamide

Adiponitrile (0.216 g), piperazine (0.172 g), $RuH_2(PPh_3)_4$ (0.069 g), water (0.077 g) and 1,2-dimethoxyethane (0.5 ml) were reacted at 180° C. in an argon gas atmosphere for 24 hours in a sealed tube. After the reaction, precipitates were separated by filtration, washed with chloroform and dried. Then, polyamide having a decomposition temperature of 230° C. was obtained in a 98% yield. Its number average molecular weight was 2,200 which was calculated in the same manner as described in Example 48. Its IR(KBR) spectrum showed absorptions at 2,930 (C—H, S), 2,870 (C—H, S), 1,635 (C=O, S), 1,435 (S), 1 250 (m), 1,205 (m) and 1,015 (m) $cm^{-1}$; and $^1H$ NMR ($HCO_2H$, 60 MHz): δ 0.72–1.46 (m, 4 H, —$CH_2$—), 1.52–2.37 (m, 4 H, —$CH_2CO$—) and 2.70–3.69 (m, 8 H, —$NCH_2$—).

EXAMPLE 54

Synthesis of polyhexamethylene-p-phenylenediacetamide 1,4-Phenylenediacetonitrile (0.312 g), hexamethylenediamine (0.232 g), RuH$_2$(PPh$_3$)$_4$ (0.069 g), water (0.074 g) and 1,2-dimethoxyethane (0.5 ml) were reacted at 180° C. in an argon gas atmosphere for 24 hours in a sealed tube. After the reaction, precipitates were separated by filtration, washed with chloroform and dried. Then, polyamide which did not melt at 300° C. was obtained in a 93% yield. Its number average molecular weight was 14,000 which was calculated in the same manner as described in Example 48. Its IR(KBr) spectrum showed absorptions at 3,250 (N—H, m), 2,920 (C—H, s), 2,850 (C—H, m), 1,630 (C=O, s), 1,530 (N—H, m), 1,425 (m) and 740 (m) cm$^{-1}$.

As is clear from the foregoing Examples, the use of metal compound catalysts, such as ruthenium compounds and the like according to the present invention, enables amides to be efficiently prepared directly from nitriles, amines and water, whereby a single step process is provided so that curtailment of reaction time, compaction of equipment and clean operations can be realized as compared with the conventional two step process for amide synthesis. In particular, the advantage of the present invention lies in the fact that the reaction can be effected under neutral conditions with a small amount of water, which is profitable energetically. Further, by using dinitriles and diamines, or aminonitriles according to the present invention, polyamides can be produced with a single step manufacturing process.

While there has been shown and described what are considered the preferred embodiments of the invention, it will be obvious to those skilled in the art that various alterations and modifications may be made therein without departing from the scope of the invention as defined by the appended claims.

What is claimed is:

1. A process for preparing a polyamide from a carbonitrile and an amine which comprises reacting by heating a mixture of a carbonitrile, an equivalent amount of an amine, which amine is a primary amine or a secondary amine, and at least a stoichiometric amount of water in the presence of an effective amount of a catalyst,
   wherein said carbonitrile is a dinitrile represented by the general formula:

R$^4$(CN)$_2$, where R$^4$ denotes a bivalent residue of:
   a. a saturated aliphatic hydrocarbon;
   b. an unsaturated aliphatic hydrocarbon;
   c. a group derived from a saturated aliphatic hydrocarbon or an unsaturated aliphatic hydrocarbon by substituting an aromatic group, a heterocyclic ring-containing group, or a heteroatom-containing group for one hydrogen atom thereof;
   d. an alicyclic hydrocarbon;
   e. an aromatic hydrocarbon;
   f. a heterocyclic compound; or
   g. a group consisting of two aliphatic hydrocarbon moieties bridged by an aromatic group, heterocyclic group, or a heteroatom,
   wherein said amine is a diamine represented by the general formula:

HN(R$^5$)—R$^6$—(R$^7$)NH, where R$^5$ and R$^7$ are the same or different and, respectively, denote a hydrogen atom or a monovalent residue of:
   a. a saturated aliphatic hydrocarbon;
   b. an unsaturated aliphatic hydrocarbon;
   c. a group derived from a saturated aliphatic hydrocarbon or an unsaturated aliphatic hydrocarbon by substituting an aromatic group for one hydrogen atom thereof;
   d. an alicyclic hydrocarbon;
   e. an aromatic hydrocarbon;
   f. a heterocyclic compound; or
   g. an aliphatic hydrocarbon having a heterocyclic ring-containing substituent or a heteroatom-containing substituent, and where R$^6$ denotes a bivalent residue of:
   a. a saturated aliphatic hydrocarbon;
   b. an unsaturated aliphatic hydrocarbon;
   c. a group derived from a saturated aliphatic hydrocarbon or an unsaturated aliphatic hydrocarbon by substituting an aromatic group, a or heterocyclic ring-containing group, or a heteroatom-containing group for one hydrogen atom thereof;
   d. an alicyclic hydrocarbon;
   e. an aromatic hydrocarbon;
   f. a heterocyclic compound; or
   g. a group consisting of two aliphatic hydrocarbon moieties bridged by an aromatic group, a heterocyclic group, or a heteroatom, and
   wherein said polyamide has a recurring unit represented by the general formula:

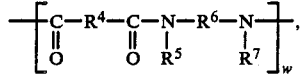

where w is an interger, and
   wherein said catalyst is comprised of a complex containing at least one metal selected from the group consisting of ruthenium, rhodium and molybdenum, and at least one group selected from the group consisting of hydride, phosphine, carbonyl, ammonia, and hydroxyl.

2. The process according to claim 1, wherein said dinitrile is an alkylenedinitrile having the general formula:

NC(CH$_2$)$_n$CN, where n is an interger ranging from 1 to 20,
   wherein said diamine is an alkylenediamine having the general formula:

HN(R$^5$)—(CH$_2$)$_m$—NHR$^7$, where m is an integer ranging from 1 to 20, and
   wherein said polyamide is a nylon-m.n+2 having a recurring unit represented by the general formula:

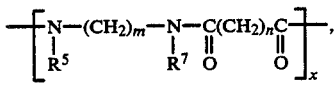

where x is an integer.

3. The process according to claim 1, wherein the catalyst is a ruthenium complex.

4. The process according to claim 3, wherein the catalyst is of the formula $RuH_2(P\text{-phenyl}_3)_4$ or $RuH_2(CO)(P\text{-phenyl}_3)_3$.

5. The process according to claim 1, wherein the catalyst is a rhodium complex.

6. The process according to claim 5, wherein the catalyst is of the formula $Rh(CO)(OH)(P\text{-phenyl}_3)_2$.

7. A process for preparing a polyamide from a carbonitrile and an amine which comprises reacting by heating a mixture of a carbonitrile, an equivalent amount of an amine, which amine is a primary amine or a secondary amine, and at least a stoichiometric amount of water in the presence of an effective amount of a catalyst, wherein said carbonitrile is a dinitrile represented by the general formula:

$$R^4(CN)_2,$$

where $R^4$ denotes:
a. a first organic group having up to 20 carbon atoms and being selected from the group consisting of an alkylene group, an alkenylene group, an alkynylene group, a cycloalkylene group and an arylene group;
b. a bivalent residue of a first 3- to 7-membered heterocyclic group having in the ring up to 3 heteroatoms selected from the group consisting of O, N, S, and mixtures thereof; or
c. a group consisting of two aliphatic hydrocarbon moieties, each said aliphatic hydrocarbon moiety having up to 10 carbon atoms and being bridged by: a phenylene group, a bivalent residue of a second 3- to 7-membered heterocyclic group having in the ring up to 3 heteroatoms selected from the group consisting of O, N, S, and mixtures thereof, or a heteroatom selected from the group consisting of O, N and S, wherein at least one hydrogen atom of any of the above is substituted with:
a second organic group having up to 12 carbon atoms and being selected from the group consisting of an aryl group, an alkenyl group, an alkynyl group; a monovalent residue of a 3- to 7-membered heterocyclic group; an OR group; a $CO_2R$ group; an $NR_2$ group; an SR group; an $SiR_3$ group; or a $CONR_2$ group, where R represents an alkyl group having up to 10 carbon atoms, a substituted alkyl group having up to 10 carbon atoms, or a phenyl group, wherein said amine is a diamine represented by the general formula:

$$HN(R^5)\text{—}R^6\text{—}(R^7)NH,$$

where $R^5$ and $R^7$ are the same or different, and, respectively, denote:
a. a hydrogen atom;
b. a third organic group having up to 20 carbon atoms and being selected from the group consisting of an alkyl group, an alkenyl group, an alkynyl group, a cycloalkyl group and an aryl group; or
c. a monovalent residue of a 3- to 7-membered heterocyclic group having in the ring up to 3 heteroatoms selected from the group consisting of O, N, S, and mixtures thereof, wherein at least one hydrogen atom of any of the above is substituted with:
a fourth organic group having up to 12 carbon atoms and being selected from the group consisting of an aryl group, an alkenyl group, and an alkynyl group; a monovalent residue of a 3- to 7-membered heterocyclic group; an OR group; a $CO_2R$ group; an $NR_2$ group; an SR group; an $SiR_3$ group; or a $CONR_2$ group; where R represents an alkyl group having up to 10 carbon atoms, a substituted alkyl group having up to 10 carbon atoms, or a phenyl group, and where $R^6$ is the same as $R^4$, and wherein said polyamide has a recurring unit represented by the general formula:

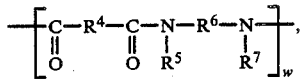

where w is an integer, and
wherein said catalyst is comprised of a complex containing at least one metal selected from the group consisting of ruthenium, rhodium and molybdenum, and at least one group selected from the group consisting of hydride, phosphine, carbonyl, ammonia, and hydroxyl.

8. The process according to claim 7, wherein the catalyst is a ruthenium complex.

9. The process according to claim 8, wherein the catalyst is of the formula $RuH_2(P\text{-phenyl}_3)_4$ or $RuH_2(CO)(P\text{-phenyl}_3)_3$.

10. The process according to claim 7, wherein the catalyst is a rhodium complex.

11. The process according to claim 10, wherein the catalyst is of the formula $Rh(CO)(OH)(P\text{-phenyl}_3)_2$.